(12) United States Patent
Safai

(10) Patent No.: US 10,572,989 B2
(45) Date of Patent: Feb. 25, 2020

(54) CHOPPED FIBER ADDITIVE MANUFACTURING VOID DETECTION

(71) Applicant: The Boeing Company, Chicago, IL (US)

(72) Inventor: Morteza Safai, Newcastle, WA (US)

(73) Assignee: THE BOEING COMPANY, Chicago, IL (US)

(*) Notice: Subject to any disclaimer, the term of this patent is extended or adjusted under 35 U.S.C. 154(b) by 106 days.

(21) Appl. No.: 16/001,666

(22) Filed: Jun. 6, 2018

(65) Prior Publication Data
US 2019/0378268 A1     Dec. 12, 2019

(51) Int. Cl.
| | |
|---|---|
| *G06K 9/00* | (2006.01) |
| *G06T 7/00* | (2017.01) |
| *H04N 5/247* | (2006.01) |
| *G06T 7/13* | (2017.01) |
| *G06T 5/00* | (2006.01) |

(Continued)

(52) U.S. Cl.
CPC ............ *G06T 7/0008* (2013.01); *B33Y 50/00* (2014.12); *G06T 5/002* (2013.01); *G06T 5/10* (2013.01); *G06T 7/001* (2013.01); *G06T 7/13* (2017.01); *G06T 7/62* (2017.01); *H04N 5/247* (2013.01);

(Continued)

(58) Field of Classification Search
CPC combination set(s) only.
See application file for complete search history.

(56) References Cited

U.S. PATENT DOCUMENTS

| | | | |
|---|---|---|---|
| 8,442,301 B2 * | 5/2013 | Dragovich | G01N 23/046 382/152 |
| 9,117,267 B2 * | 8/2015 | Francis, Jr. | G01B 11/2513 |

(Continued)

FOREIGN PATENT DOCUMENTS

| | | |
|---|---|---|
| EP | 2749869 A1 | 7/2014 |
| EP | 3269535 A1 | 1/2018 |

OTHER PUBLICATIONS

Wan et al., "Micro-CT Analysis of Internal Geometry of Chopped Carbon Fiber Tapes Reinforced Thermoplastics," Composites Part A, 91 (2016) 211-231.

(Continued)

*Primary Examiner* — Gregory M Desire
(74) *Attorney, Agent, or Firm* — MH2 Technology Law Group LLP

(57) ABSTRACT

According to various examples, techniques for detecting an off specification void in an item produced by an additive manufacturing process are presented. The techniques can utilize a system that includes cameras positioned to capture images of deposition of material in an additive manufacturing receptacle from multiple angles. The system can include at least one hardware electronic feature detector hard coded to detect features of elements of the material in image data derived from images. The system can further includes at least one electronic processor configured to perform a method of receiving feature data from the at least one hardware electronic feature detector, generating an electronic three-dimensional representation of the material in the additive manufacturing receptacle from the feature data, determining from the electronic three-dimensional representation of the material in the additive manufacturing receptacle that an off specification void exists, and providing an alert.

20 Claims, 5 Drawing Sheets

(51) Int. Cl.
  *G06T 5/10*   (2006.01)
  *B33Y 50/00*  (2015.01)
  *G06T 7/62*   (2017.01)

(52) U.S. Cl.
  CPC .............. *G06T 2207/20216* (2013.01); *G06T 2207/30108* (2013.01)

(56) References Cited

U.S. PATENT DOCUMENTS

| | | | |
|---|---|---|---|
| 9,731,455 B2* | 8/2017 | Meredith | ............. B29C 31/085 |
| 2015/0273583 A1 | 10/2015 | Bumgardner | |
| 2018/0243800 A1* | 8/2018 | Kumar | ................. B07C 5/3416 |

OTHER PUBLICATIONS

Extended European Search Report dated Jul. 30, 2019 in corresponding European Application No. 19178295.2 (10 pages).

Chen, J. et al., "Real-time Edge-Aware Image Processing with the Bilateral Grid," ACM SIGGRAPH 2007 conference, pp. 1-9.

Kaestner, A. et al., "Imaging and Image Processing in Porous Media Research", Advances in Water Resources, 2008, vol. 31, pp. 1174-1187.

Soulaine, C. et al., "The impact of sub-resolution porosity of X-ray microtomography images on the permeability", pp. 1-19.

Meola, C. et al., "Flash Thermography to Evaluate Porosity in Carbon Fiber Reinforced Polymer (CFRPs)", Materials, 2014, vol. 4, pp. 1483-1501.

Sturm, L. et al. "In-situ Detection of Build Defects in Additive Manufacturing via Impedance-Based Monitoring," Proceedings of the 27th Annual International Solid Freeform Fabrication Symposium, 2016, pp. 1458-1478.

* cited by examiner

CHOPPED FIBER ADDITIVE MANUFACTURING VOID DETECTION

FIELD

This disclosure relates generally to manufacturing processes that utilize chopped fiber or other generally chip-shaped materials.

BACKGROUND

Chopped fiber material, such as chopped carbon fiber chips, is used in the build-up of manufactured items according to some additive manufacturing processes. Such processes can result in undesirable porosity, making an item unusable. Off specification porosity typically cannot be determined until the final item is made, cured, and tested, e.g., by using computer tomography ("CT") to image the internal structure of the item. This can result in lost time, money, and materials, particularly if the problem is due to a manufacturing process that is not corrected until after additional faulty items have already been produced.

SUMMARY

According to various examples, a system for detecting an off specification void in an item produced by an additive manufacturing process is provided. The system includes a first camera positioned to capture a first plurality of images of deposition of material in an additive manufacturing receptacle from a first angle; a second camera positioned to capture a second plurality of images of deposition the material in the additive manufacturing receptacle from a second angle; at least one hardware electronic feature detector communicatively coupled to the first camera and to the second camera, the hardware electronic feature detector hard coded to detect features of elements of the material in image data derived from the first plurality of images and in the second plurality of images; at least one electronic triangulator communicatively coupled to the at least one hardware electronic feature detector and configured to: receive feature data from the at least one hardware electronic feature detector; and generate an electronic three-dimensional representation of the material in the additive manufacturing receptacle from the feature data; at least one electronic void detector configured to determine from the electronic three-dimensional representation of the material in the additive manufacturing receptacle that an off specification void exists in the additive manufacturing receptacle; and at least one display configured to provide an alert that an off specification void exists in the additive manufacturing receptacle.

Various optional features of the above embodiments include the following. The material can include chopped fiber chips. The at least one hardware electronic feature detector can be further configured to detect edges of a plurality of individual chopped fiber chips. The at least one electronic void detector can be further configured to: compute volumes of a plurality of chopped fiber chips; and compute void information from the volumes, wherein the void information represents a size of at least one void in the additive manufacturing receptacle. The alert can include a direction to empty the additive manufacturing receptacle. The system can include noise reducers configured to perform a Fourier transform to reduce noise in the first plurality of images and in the second plurality of images. The additive manufacturing receptacle can include a mold. The system can include averagers configured to perform an averaging of pluralities of captured images. The system can include a laser configured to direct light pulses at the deposition of material in the additive manufacturing receptacle, wherein a duration of the light pulses is less than twice an integration time of the first camera and the second camera. The first camera and the second camera can be configured to capture the images of deposition of the material in the additive manufacturing receptacle at a rate of at least 5000 images per second.

According to various embodiments, a method of detecting an off specification void in an item produced by an additive manufacturing process is presented. The method includes capturing a first plurality of images, by a first camera and from a first angle, of deposition of material in an additive manufacturing receptacle; capturing a second plurality of images, by a second camera and from a second angle, of deposition the material in the additive manufacturing receptacle; detecting, by at least one hardware electronic feature detector communicatively coupled to the first camera and to the second camera and hard coded to detect features of elements of the material, feature data from image data derived from the first plurality of images and from the second plurality of images; generating, by at least one electronic triangulator communicatively coupled to the hardware electronic feature detector, an electronic three-dimensional representation of the material in the additive manufacturing receptacle from the feature data; determining from the electronic three-dimensional representation of the material in the additive manufacturing receptacle, that an off specification void exists in the additive manufacturing receptacle; and providing an alert that an off specification void exists in the additive manufacturing receptacle.

Various optional features of the above examples include the following. The material can include chopped fiber chips. The feature data can include representations of edges of a plurality of individual chopped fiber chips. The method can include computing volumes of a plurality of chopped fiber chips; and computing void information from the volumes, wherein the void information represents a size of at least one void in the additive manufacturing receptacle. The alert can include a direction to empty the additive manufacturing receptacle. The method can further include removing noise in the first plurality of images and in the second plurality of images. The additive manufacturing receptacle can include a mold. The method can include deriving the image data from the first plurality of images and from the second plurality of images by averaging subsets of images of the first plurality of images and by averaging subsets of images of the second plurality of images. The method can include directing, by a laser, light pulses at the deposition of material in the additive manufacturing receptacle, wherein a duration of the light pulses is less than twice an integration time of the first camera and the second camera. The capturing, by the first camera, and the capturing, by the second camera, can each include capturing the images of the deposition of the material in the additive manufacturing receptacle at a rate of at least 5000 images per second.

BRIEF DESCRIPTION OF THE DRAWINGS

Various features of the examples can be more fully appreciated, as the examples become better understood with reference to the following detailed description, when considered in connection with the accompanying figures, in which:}

DESCRIPTION

Reference will now be made in detail to the disclosed examples, which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific examples. These examples are described in sufficient detail to enable those skilled in the art to practice them and it is to be understood that other examples may be utilized and that changes may be made without departing from the scope of the disclosure. The following description is, therefore, merely exemplary.

Figure 1:
FIG. 1 is a magnified image of chopped fiber material suitable for use in an additive manufacturing process according to various examples.

FIG. 1 is a magnified image 100 of chopped fiber chips 102 suitable for use in an additive manufacturing process according to various examples. (Chopped fiber chips 102 are also known in the art as "chopped fiber flakes".) Chopped fiber chips may formed from carbon fibers or other fibrous material. Chopped fiber chips have profiles generally shaped as squares, rectangles, parallelograms, trapezoids (with the parallel sides running in the direction of the fibers) and/or quadrilaterals. Chopped fiber chips generally have a thickness in the dimension perpendicular to the profile faces that is shorter than any profile face side. The thickness of the dimension perpendicular to the profile faces may range in size from 1 mm (or less, for carbon fiber chips, for example), to 1 cm or more. The edges of the profile faces may range in size from 5 mm to 5 cm or more, for some applications.

In general, chopped fiber chips 102 can be deposited in an additive manufacturing receptacle, such as a mold or shell, to form an item. (An example of an additive manufacturing mold and an additive manufacturing shell are shown and described below in reference to FIG. 5.) In more detail, chopped fiber chips 102 may be dropped on top of each other into the receptacle, then compacted, heated, and cured. A shaker table may be used to hold the receptacle and assist in compacting the chopped fiber chips 102. If the receptacle is a mold, then the item may be removed and utilized; if the receptacle is a shell, then the shell may remain as part of the item, which may then be removed and utilized.

During the manufacturing process, chopped fiber chips 102 may be deposited into the receptacle by releasing them above the receptacle, such that the force of gravity conveys them into the receptacle. A conveyer belt or other manufacturing system may be used to that end. Chopped fiber chips 102 lay down differently with every chip and do not generally coalesce into regular or semi-regular patterns as with other types of polymeric or metal powders (e.g., those with generally spherical elements). Therefore, items manufactured according to this process have a non-zero percentage of porosity, i.e., empty space.

Once the manufacturing of an item is completed, if there is too much porosity, e.g., for structural integrity, then the item may not be useable. According to existing non-destructive void detection techniques such as the use of CT, the unacceptable void might not be detected until after the manufacturing process for the item, including compacting, heating, and curing, is complete. In that timeframe, however, according to existing techniques, the manufacturing process may continue and additional receptacles may be improperly filled, and the chopped fiber chips compacted, heated, and even cured, before it is recognized there is a processing problem. Thus, techniques for real-time detection of off specification voids in additive manufactured items would be highly useful to substantially reduce wasted time, energy, money, and materials.

Naïve approaches to the problem of real time detection of voids (e.g., off specification voids) that rely on capturing images of the chopped fiber would generate a very large amount of data that cannot be processed in the real time. For example, for an image that is 5000×5000 pixels, such that each computer readable image is 25 MB, an image capture rate of 5000 images per second would result in 125 terabytes of captured image data per second, or 7.5 petabytes per minute. This magnitude of data cannot be processed to detect voids in real time in the present context using existing techniques. Thus, a problem in the real-time imaging and analysis of additive manufactured items exists that known techniques cannot address. Some examples solve this, and other, problems through the use of various specialized equipment and techniques as discussed herein.

Figure 2:
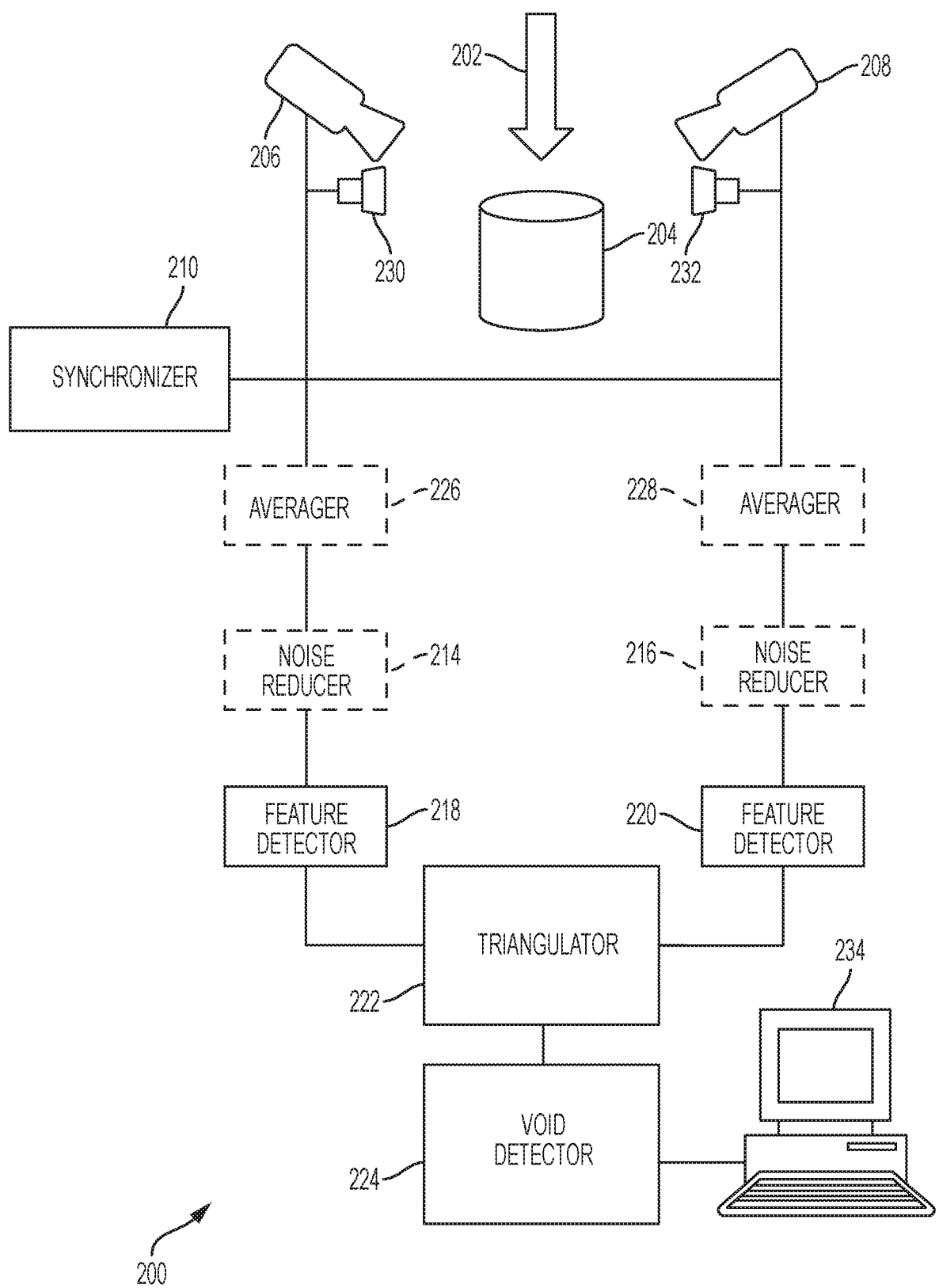
FIG. 2 is a schematic diagram of a system for detecting off specification voids in a chopped fiber additive manufactured item according to various examples.

FIG. 2 is a schematic diagram of a system 200 for detecting off specification voids in a chopped fiber additive manufactured item according to various examples. As depicted, system 200 detects voids in items manufactured according to a process that includes depositing material 202, such as chopped fiber chips 102, into additive manufacturing receptacle 204. Subsequently, the assembled additive manufacturing receptacle 204 and its included material 202 can be subjected to compacting, heating, and curing. Additive manufacturing receptacle 204 can be a mold, from which the item is removed, or a shell, which remains as an outer layer of the item. Material 202 can be brought to additive manufacturing receptacle 204 by conveyer belt, hopper, or other manufacturing technique, and deposited into additive manufacturing receptacle 204 by the force of gravity. Additive manufacturing receptacle 204 can be held on a conveyer belt, shaker table, or other manufacturing device.

System 200 includes first camera 206 and second camera 208. Cameras 206, 208 can capture images with a resolution of, for example, 5000×5000 pixels. Cameras 206, 208 can have an associated integration time (i.e., the duration of image capture) in the range of 5-500 microseconds in order to support an image capture rate of 2,000-200,000 images per second. Cameras 206, 208 can be positioned to capture images of material 202 as it is deposited in additive manufacturing receptacle 204. In particular, cameras 206, 208 can be positioned so as to capture images of the same space but from different angles, so as to enable triangulation of the position of items captured in images by both cameras 206, 208 simultaneously. An example triangulation process is described below in reference to triangulator 222. The outputs of cameras 206, 208 are coupled to averagers 226, 228, respectively.

Averagers 226, 228 average together output images of cameras 206, 208, respectively, in batches. Averagers 226, 228 are optional in some examples. In examples with averagers 226, 228, sequential sets of images (e.g., sets of any number of images from 2 to 10) are averaged together pixel-wise, and then the averaged images are output. Averagers 226, 228 can include fast electronic memory, e.g., random access memory ("RAM") for temporarily storing batches of images for purposes of averaging. The averaging can be performed by averaging hardware rather than software, for speed, in order to handle image captures by cameras 206, 208 at a rate of between 2,000 and 200,000 images per second. Averagers can be present in cameras 206, 208, or coupled to outputs of cameras 214, 216, according to various examples. The outputs of averagers 226, 228 are coupled to inputs of respective noise reducers 214, 216.

Noise reducers 214, 216 accept images and remove noise therefore in real time. The accepted images can be output from cameras 206, 208 or output from averagers 226, 228, according to various examples. Noise reducers 214, 216 can implement a fast Fourier transform in hardware (as opposed to software), apply a hardware-implemented low-pass filter to remove noise, and reverse the transform using a hardware-implemented reverse Fourier transform. According to some examples, noise reducers 214, 216 are implemented in hardware, because software implementations may not be sufficiently fast to process images in real time at the desired rate (e.g., 2,000-200,000 images per second). Outputs of noise reducers 214, 216 are coupled to inputs of respective feature detectors 218, 220.

Feature detectors 218, 220 detect features in received images and output feature data representing the detected features. Feature detectors can input image data from any of cameras 206, 208, averagers 226, 228, or noise reducers 214, 216, according to various examples. That is, feature detectors 218, 220 detect features in image data derived from images captured by cameras 208, 208, respectively, either raw, as processed by averagers 226, 228, respectively, and/or as processed by noise reducers 214, 216, respectively.

Example suitable features detected by feature detectors 218, 220 according to various examples include edges. In such examples, feature detectors 218, 220 can include edge detectors. Examples of suitable, known, real time edge detection processes are disclosed in, for example, Chen, et al., Real-time Edge-Aware Image Processing with the Bilateral Grid, *ACM Transactions on Graphics*, Proceedings of the ACM SIGGRAPH 2007 Conference, as well as at www.embedded-vision.com/platinum-members/bdti/embedded-vision-training/documents/pages/building-machines-see-finding-edges-i. An example known edge detection process includes removing image noise using a Gaussian filter, calculating an intensity gradient, applying non-maximum suppression to clarify lines, and applying hysteresis to filter out undesirable pixels. However, other edge detection techniques may be applied in the alternative by feature detectors 218, 220. Feature detectors 218, 220 are, according to some examples, capable of detecting edges of discrete components of material 202 as they appear in images captured by cameras 206, 208 (possibly having been subjected to averagers 226, 228 and/or noise reducers 214, 216) in real time. Other suitable features for detection may include corners and faces. Such features can be used instead of, or in addition to, edges.

Note that many examples do not utilize features like color or aesthetics, so the entire images produced by cameras 206, 208, which may be on the order of 25 MB, are not needed. Instead, examples can utilize edge information to determine a volume, and location within additive manufacturing receptacle 204, of each chopped fiber chip 202. Therefore, feature detectors 218, 220 can input image data produced by cameras 206, 208, respectively, possibly processed by one or both of averagers 226, 228 and/or noise reducers 214, 216, and output feature data representing the detected features, their dimensions, and their locations within additive manufacturing receptacle 204. Thus, some examples substantially reduce the amount of data processed in order to detect off specification voids. By reducing a 25 MB image to 250 KB of feature data, for example, the data can be used to get a very efficient and accurate volumetric measurement of the material 202 within additive manufacturing receptacle 204.

Feature detectors 218, 220 can be implemented in hardware, e.g., CMOS, as opposed to software, for fast implementation. Feature detectors 218, 220 (as well as any of noise reducers 214, 216, and/or averagers 226, 228, if present) can be implemented on board respective cameras 206, 208. The outputs of feature detectors 218, 220 are coupled to the inputs of triangulator 222.

Triangulator 222 accepts feature data from feature detectors 218, 220 and determines location data for substantially all material 202 deposited in additive manufacturing receptacle 204. In particular, using known feature processing triangulation techniques, triangulator 222 determines a location of each discrete component of material 202. Triangulator 222 can further determine an orientation for each such chip. Using the detected edges, possibly in combination with known chopped fiber chip widths, triangulator 222 determines a volume of each such chip using standard multiplication. (According to other examples, such volume determinations are performed by void detector 224, or another system component, instead.) Triangulator 222 outputs a three-dimensional representation of material 202 present in additive manufacturing receptacle 204, including, for each such chip, one or more of its location, volume, and/or orientation. The three-dimensional representation can be in any of a variety of formats, such as, by way of non-limiting examples, stereo CAD-3D 2.0 Image File (0.3D20) or 3D Format (0.3DF) or gITF 3D2 Studio_Autodesk and FBX—Autodesk. Triangulator 222 may be implemented in hardware, e.g., CMOS, as opposed to software, for fast implementation. The output of triangulator 222 is coupled to an input to void detector 224.

Void detector 224 accepts a three-dimensional representation of material 202 present in additive manufacturing receptacle 204 from triangulator 222 and determines whether an off specification void exists in the represented item. Criteria for such a determination include, for example, that a total volume occupied by material 202 is less than some predetermined total volume threshold, or that a size of a largest void exceeds some predetermined largest volume threshold. Values for such thresholds vary according to the particular manufactured item and its intended use. Void size may be characterized using a variety of metrics, e.g., the diameter of the largest sphere that can be present in the additive manufacturing receptacle without touching any chopped fiber chip or the additive manufacturing receptacle. Void detector 224 can output an alert if the determination indicates that an off specification void exists. The alert can be a message, a single bit value, or a changed bit value indicating an off specification void among a stream of bit values indicating acceptable items, each bit value corresponding to a particular item. Void detector 224 can provide the alert to display 234, to a different human interface, or to a machine in the manufacturing process.

Display 234 can be a computer screen, a mobile device screen, or another type of display capable of alerting a human user in real time to a detected off specification void in a manufactured item. According to some examples, display 234 can include or be replaced by an audio output device, such as a speaker, which may produce a sound representing the alert. Other expedients for conveying an alert to a human user are also possible in the alternative or in addition.

System 200 also includes laser 230 and laser 232. Lasers 230, 232 are positioned to illuminate the deposition of chopped fiber chips 204 in additive manufacturing receptacle 204 for image capture by cameras 206, 208. Wavelengths of lasers 230, 232 may be selected for the particular additive manufacturing process and materials. For example, the wavelength may be selected to be reflected by the additive manufacturing material and absorbed by machine parts of the manufacturing system itself. Lasers 230, 232, as well as cameras 206, and other portions of system 200, are controlled by synchronizer 210.

Synchronizer 210 controls and coordinates much of the operation of system 200. Synchronizer 210 is communicatively coupled to any, or any combination, of cameras 206, 208, to lasers 230, 232, to triangulator 222, and to void detector 224, according to various examples. Note that synchronizer may be communicatively coupled to any of these systems using a different communication channel from that which conveys image data, according to some examples. Synchronizer 210 generates synchronization pulses, which are electrical signals that trigger actions by the coupled system components. Synchronizer 210 provides timing pulses to the various system components to coordinate operation of the overall system, thereby enabling very fast, real time void detection in additive manifesting processes. The operation of synchronizer 210, as well as the relative arrangement of its synchronization pulses, is described in detail below in reference to FIG. 3.

Figure 3:
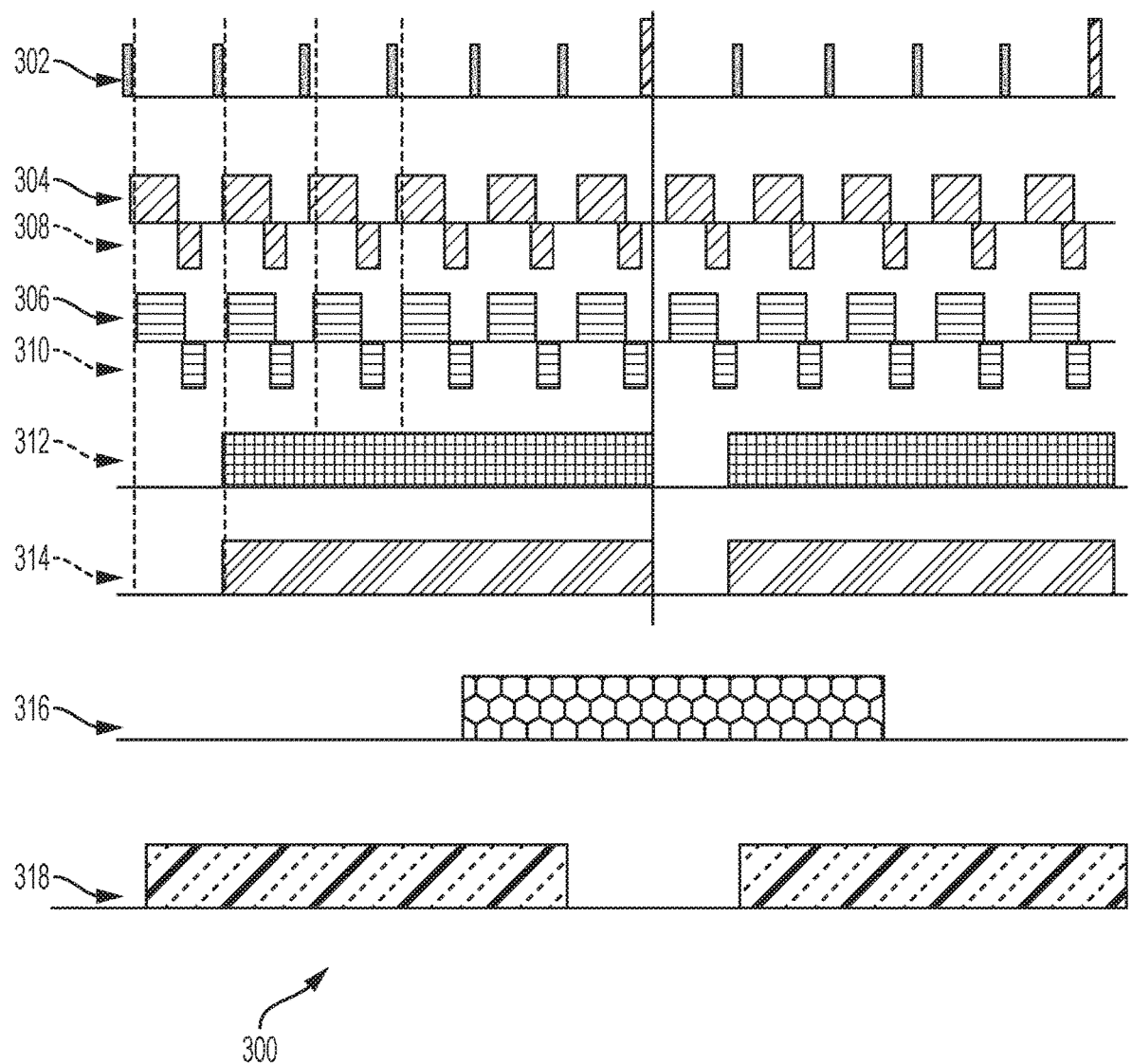
FIG. 3 is a timing diagram for a system for detecting off specification voids in a chopped fiber additive manufactured item according to various examples.

FIG. 3 is a timing diagram 300 for a system (e.g., system 200) for detecting off specification voids in a chopped fiber additive manufactured item according to various examples. Timing diagram 300 depicts relative timing for, and relative durations of, synchronization pulses 302 and various actions performed by cameras 206, 208, lasers 230, 232, averagers 226, 228, triangulator 222, and void detector 224.

As depicted in timing diagram 300, synchronizer 210 generates and passes to cameras 206, 208 and lasers 230, 232 synchronization pulses 302. Synchronization pulses 302 may be generated at any rate, e.g., between 2,000 and 200,000 pulses per second. Synchronization pulses 302 can include 5 volt pulses sent to the various systems. Synchronization pulses 302 can trigger image captures by cameras 206, 208 and illumination by lasers 230, 232.

Also depicted in timing diagram 300 are integration intervals 304 for camera 206, integration intervals 306 for camera 208, data transfer intervals 308 for camera 206, and data transfer intervals 310 for camera 208. Each block depicted in integration intervals 304, 306 represents the duration of the temporal interval within which the respective camera 206, 208 captures an image. The duration of illumination by lasers 230, 232, is about as long, or slightly longer, than the integration time of cameras 206, 208 (e.g., between 90% and 190% of the integration time). In such examples, cameras 206, 208 may lack shutters. Immediately following each block depicted in integration intervals 304, 306 are blocks depicting data transfer intervals 308, 310 for cameras 206, 208, respectively. Such blocks represent the duration of the temporal interval within which the respective camera 206, 208 transfers its image data to the next system component, whether it be averagers 226, 228, noise reducers 214, 216, or feature detectors 218, 220. Note that the timing of the various system components depicted in timing diagram 300, particularly the handling of integration intervals 304 for camera 206 and integration intervals 306 for camera 208 relative to the other timing actions, together with the substantial memory reduction provided by feature detectors 218, 220, permit the system to operate in real time to detect voids in an additive manufacturing process.

Also depicted in timing diagram 300 are averaging, noise reducing, and feature detecting intervals 312 for camera 206, and averaging, noise reducing, and feature detecting intervals 314 for camera 208. Note that synchronizer 210 can direct averagers 226, 228 to average image data in batches. In particular, synchronizer passes timing pulses to averagers 226, 226 that trigger averagers to pixel-wise average batches of images. Thus, synchronizer 210 can dispatch triggering pulses to averagers 226, 228 after every N synchronization pulses 203, where N can be any number between 2 and 10. According to other examples, synchronizer 210 can dispatch synchronization pulses 302 to averagers 226, 228, which are triggered by every N-th synchronization pulse 203. Regardless as to the particular triggering event, upon triggering, averagers 226, 228 retrieve the previous N or N−1 images from their respective memories and perform the pixel-wise averaging thereupon. For the non-limiting example depicted in timing diagram 300, averagers 226, 228 average batches of five images, thus N=5 for this non-limiting example. Note that, as depicted in timing diagram 300, averaging, noise reducing, and feature detecting intervals 312, 314 commence during, or just after, the data transfer interval for the first image of any particular batch.

Averaging, noise reducing, and feature detecting intervals 312, 314 also represent the time during which noise reducers 214, 216 perform their respective noise reduction processing, if present in the particular example.

Averaging, noise reducing, and feature detecting intervals 312, 314 also represent the time during which feature detections 218, 220 perform their respective feature detection processing.

Also depicted in timing diagram 300 is triangulation interval 316. Triangulation interval 316 represents the time interval within which triangulator 222 operates on the feature data provided by feature detectors 218, 220 to produce its three-dimensional representation.

Finally, also depicted in timing diagram 300 are volumetric processing intervals 318. Volumetric processing intervals 318 represent the time intervals within which void detector 224 process volume information to determine whether an off specification void exists based on the three-dimensional representation provided by triangulator 222, possibly in combination with volume data determined by void detector 224. At the end of each of volumetric processing intervals 318, void detector 224 can indicate to display 234 (or other system component) whether such processing indicates that an off specification void exists.

Figure 4:
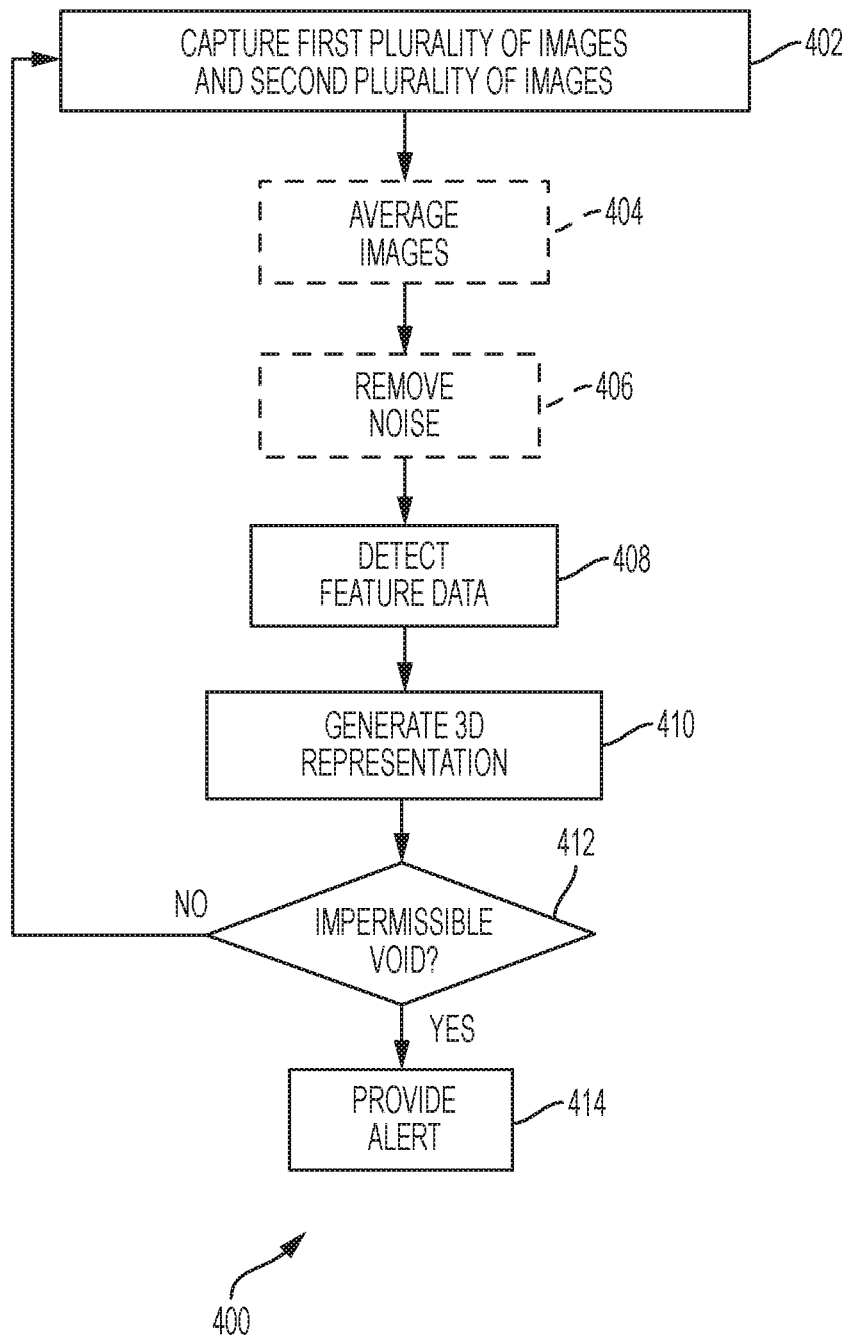
FIG. 4 is a flow diagram for a method of detecting off specification voids in a chopped fiber manufacturing process according to various examples.

FIG. 4 is a flow diagram for a method 400 of detecting voids in a chopped fiber manufacturing process according to various examples. Method 400 can be implemented using system 200 of FIG. 2, with the system components' timing as illustrated by timing diagram 300 of FIG. 3, for example.

At block 402, camera 206 captures a first plurality of images, and camera 208 captures a second plurality of images. The first plurality of images can be captured simultaneously with the second plurality of images. Each image can be captured as triggered by an illuminating laser pulse from a respective laser 230, 232. Each plurality if images can correspond to a batch of N>1 images that are to be averaged together by a respective averager 226, 228. The images are captured as the chopped fiber chips are deposited in additive manufacturing receptacle 204 as shown and described above in reference to FIG. 2. The pluralities of images are then optionally processed by one or both of averagers 226, 228 and noise reducers 214, 216, before such image data is passed to feature detectors 218, 220. Alternately, such image data is passed to feature detectors 218, 220 without being processed by averagers 226, 228 and noise reducers 214, 216.

At block 404, averagers 226, 228 pixel-wise average together batches of images received from cameras 206, 208. This process is shown and described above in reference to FIG. 2, averagers 226, 228. In particular, batches of 2, 3, 4, 5, 6, or any number of images less than 20 may be pixel-wise averaged together according to various examples.

At block 406, noise reducers 214, 216 remove noise from image data derived from the first and second pluralities of images. Noise reducers can convert the image data to the frequency domain, filter out high frequencies, and convert back to the spatial domain using hardware processing, as described above in reference to FIG. 2. The image data is then passed to feature detectors 218, 220.

At block 408, feature detectors 218, 220 detect features in the image data provided by cameras 206, 208, averagers 226, 228, or noise reducers 214, 216, depending on the particular example. The feature detectors can detect edges as shown and described above in reference to FIG. 2, feature detectors 218, 220. Feature detectors 214, 216 output feature data representing the image data that they receive and process. Feature detectors 218, 220 then pass the feature data to triangulator 222.

At block 410, triangulator 222 processes the feature data received from feature detectors 218, 220. As shown and described above in reference to FIG. 2, triangulator applies known triangulation techniques to the feature data received from feature detectors 218, 220 to generate a three-dimensional representation of material 202 present in additive manufacturing receptacle 204. In particular, the three-dimensional representation may be less than 25 KB and include one or more of location, orientation, and volume for each such chopped fiber chip. Triangulator 222 passes the three-dimensional representation to void detector 412 for further processing.

At block 412, void detector 224 determines whether a void exists in the chopped fiber additive manufacturing receptacle 204. The determination may be whether the chopped fiber additive manufacturing receptacle 204 includes a void of at least a given size. The determination may be made using any of a variety of metrics. According to some examples, the determination is made by determining whether the three-dimensional representation indicates that a void of at least a given size exists. Such a determination may be made by, for example, determining whether the chopped fiber additive manufacturing receptacle 204 could contain a sphere of a corresponding given diameter. According to other examples, the determination is made by determining whether the three-dimensional representation indicates that a total volume occupied by material 202 is less than some total volume threshold. Other determination metrics are possible within the scope of some examples.

If the determination at block 412 is "NO", then control passes back to block 402. Otherwise, if the determination at block 412 is "YES", the control passes to block 414.

At block 414, display 234 provides an alert to a user indicating that an off specification void exists in the chopped fiber manufactured item. The alert may be audible, visible, or a combination. The alert may be sent to a mobile device of the user according to some examples. The process can also stop the manufacturing line, or a portion thereof, until the item is removed and dealt with.

Figure 5:
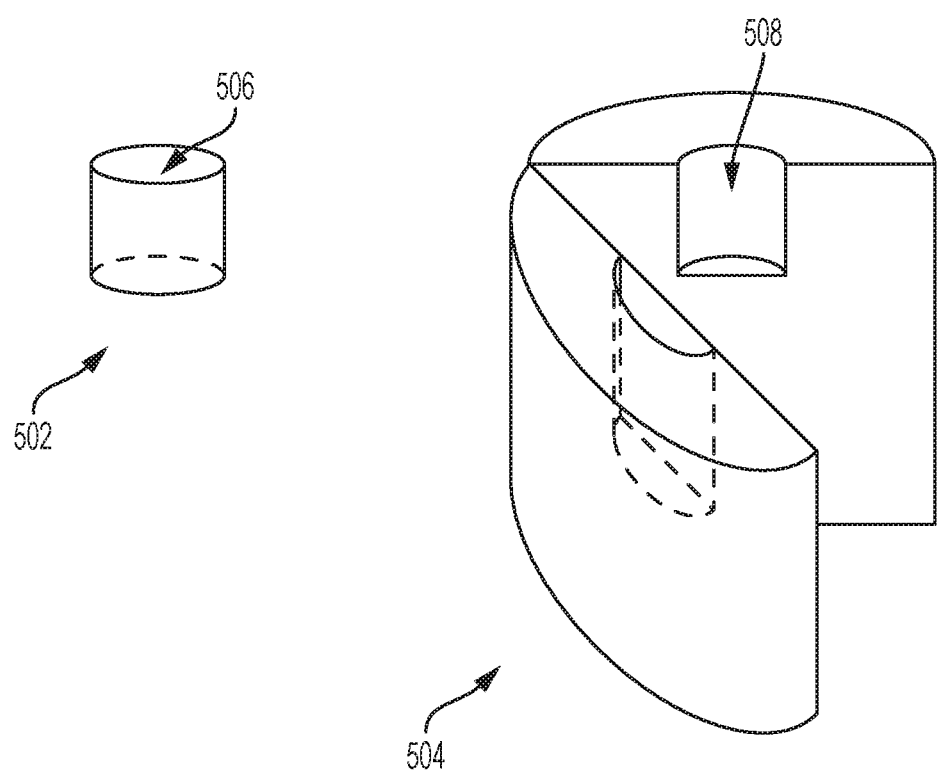
FIG. 5 is a schematic diagram of an additive manufacturing receptacle mold and an additive manufacturing receptacle shell according to various examples.

FIG. 5 is a schematic diagram of an additive manufacturing receptacle mold 504 and an additive manufacturing receptacle shell 502 according to various examples. In use, additive manufacturing shell 502 receives chopped fiber chips through opening 506. Additive manufacturing shell 502 may remain part of the manufactured component and be cured together with the chopped fiber chips. Additive manufacturing mold 504 received chopped fiber chips through opening 508. The additive manufacturing item is removed from additive manufacturing mold 504 prior to use, and additive manufacturing mold does not form part of any completed product.

Note that although exemplary examples have been describe relative to additive manufacturing processes using chopped fiber chips, examples are not so limited. The disclosed techniques may be applied to any additive manufacturing technique that uses additive manufacturing material consisting of discrete elements that include features, such as edges, that can be used to determine volumes of the elements. For example, the technique may be applied to any additive manufacturing technique that utilizes material that consists of parallelepiped shaped discrete elements.

Certain examples described above can be performed in part using a computer application or program. The computer program can exist in a variety of forms, both active and inactive. For example, the computer program can exist as one or more software programs, software modules, or both, that can be comprised of program instructions in source code, object code, executable code or other formats, firmware program(s), or hardware description language (HDL) files. Any of the above can be embodied on a computer readable medium, which can include computer readable storage devices and media in compressed or uncompressed form. Exemplary computer readable storage devices and media include conventional computer system RAM (random access memory), ROM (read-only memory), EPROM (erasable, programmable ROM), EEPROM (electrically erasable, programmable ROM), and magnetic or optical disks or tapes.

Those skilled in the art will be able to make various modifications to the described examples without departing from the true spirit and scope. The terms and descriptions used herein are set forth by way of illustration only and are not meant as limitations. In particular, although the method has been described by examples, the steps of the method can be performed in a different order than illustrated or simultaneously. Those skilled in the art will recognize that these and other variations are possible within the spirit and scope as defined in the following claims and their equivalents.

What is claimed is:

1. A system for detecting an off specification void in an item produced by an additive manufacturing process, the system comprising:
   a first camera positioned to capture a first plurality of images of deposition of material in an additive manufacturing receptacle from a first angle;
   a second camera positioned to capture a second plurality of images of deposition the material in the additive manufacturing receptacle from a second angle;
   at least one hardware electronic feature detector communicatively coupled to the first camera and to the second camera, the hardware electronic feature detector hard coded to detect features of elements of the material in image data derived from the first plurality of images and in the second plurality of images;

at least one electronic triangulator communicatively coupled to the at least one hardware electronic feature detector and configured to: receive feature data from the at least one hardware electronic feature detector; and generate an electronic three-dimensional representation of the material in the additive manufacturing receptacle from the feature data;

at least one electronic void detector configured to determine from the electronic three-dimensional representation of the material in the additive manufacturing receptacle that an off specification void exists in the additive manufacturing receptacle; and at least one display configured to provide an alert that an off specification void exists in the additive manufacturing receptacle.

2. The system of claim 1, wherein the material comprises chopped fiber chips.

3. The system of claim 2, and wherein the at least one hardware electronic feature detector is further configured to detect edges of a plurality of individual chopped fiber chips.

4. The system of claim 2, wherein the at least one electronic void detector is further configured to:
compute volumes of a plurality of chopped fiber chips; and
compute void information from the volumes, wherein the void information represents a size of at least one void in the additive manufacturing receptacle.

5. The system of claim 1, wherein the alert comprises a direction to empty the additive manufacturing receptacle.

6. The system of claim 1, further comprising noise reducers configured to perform a Fourier transform to reduce noise in the first plurality of images and in the second plurality of images.

7. The system of claim 1, wherein the additive manufacturing receptacle comprises a mold.

8. The system of claim 1, further comprising averagers configured to perform an averaging of pluralities of captured images.

9. The system of claim 1, further comprising a laser configured to direct light pulses at the deposition of material in the additive manufacturing receptacle, wherein a duration of the light pulses is less than twice an integration time of the first camera and the second camera.

10. The system of claim 1, wherein the first camera and the second camera are configured to capture the images of deposition of the material in the additive manufacturing receptacle at a rate of at least 5000 images per second.

11. A method of detecting an off specification void in an item produced by an additive manufacturing process, the method comprising:
capturing a first plurality of images, by a first camera and from a first angle, of deposition of material in an additive manufacturing receptacle;
capturing a second plurality of images, by a second camera and from a second angle, of deposition the material in the additive manufacturing receptacle;
detecting, by at least one hardware electronic feature detector communicatively coupled to the first camera and to the second camera and hard coded to detect features of elements of the material, feature data from image data derived from the first plurality of images and from the second plurality of images;
generating, by at least one electronic triangulator communicatively coupled to the hardware electronic feature detector, an electronic three-dimensional representation of the material in the additive manufacturing receptacle from the feature data;
determining from the electronic three-dimensional representation of the material in the additive manufacturing receptacle, that an off specification void exists in the additive manufacturing receptacle; and
providing an alert that an off specification void exists in the additive manufacturing receptacle.

12. The method of claim 11, wherein the material comprises chopped fiber chips.

13. The method of claim 12, and wherein the feature data comprises representations of edges of a plurality of individual chopped fiber chips.

14. The method of claim 12, further comprising:
computing volumes of a plurality of chopped fiber chips; and
computing void information from the volumes, wherein the void information represents a size of at least one void in the additive manufacturing receptacle.

15. The method of claim 11, wherein the alert comprises a direction to empty the additive manufacturing receptacle.

16. The method of claim 11, further comprising removing noise in the first plurality of images and in the second plurality of images.

17. The method of claim 11, wherein the additive manufacturing receptacle comprises a mold.

18. The method of claim 11, further comprising deriving the image data from the first plurality of images and from the second plurality of images by averaging subsets of images of the first plurality of images and by averaging subsets of images of the second plurality of images.

19. The method of claim 11, further comprising directing, by a laser, light pulses at the deposition of material in the additive manufacturing receptacle, wherein a duration of the light pulses is less than twice an integration time of the first camera and the second camera.

20. The method of claim 11, wherein the capturing, by the first camera, and the capturing, by the second camera, each comprise capturing the images of the deposition of the material in the additive manufacturing receptacle at a rate of at least 5000 images per second.

* * * * *